United States Patent
Dacosta et al.

(10) Patent No.: US 9,848,893 B2
(45) Date of Patent: Dec. 26, 2017

(54) BONE IMPLANTS AND CUTTING APPARATUSES AND METHODS

(71) Applicant: PARAGON 28, INC., Englewood, CO (US)

(72) Inventors: Albert Dacosta, Lone Tree, CO (US); Matthew S. Solar, Indialantic, FL (US); Thomas Chang, Santa Rosa, CA (US); Michael Houghton, Fort Collins, CO (US)

(73) Assignee: PARAGON 28, INC., Englewood, CO (US)

( * ) Notice: Subject to any disclaimer, the term of this patent is extended or adjusted under 35 U.S.C. 154(b) by 0 days.

(21) Appl. No.: 15/260,836

(22) Filed: Sep. 9, 2016

(65) Prior Publication Data

US 2016/0374695 A1    Dec. 29, 2016

Related U.S. Application Data

(62) Division of application No. 14/110,536, filed as application No. PCT/US2012/032765 on Apr. 9, 2012, now Pat. No. 9,452,057.

(Continued)

(51) Int. Cl.
*A61F 2/42* (2006.01)
*A61B 17/16* (2006.01)
(Continued)

(52) U.S. Cl.
CPC ...... *A61B 17/1682* (2013.01); *A61B 17/1739* (2013.01); *A61F 2/4225* (2013.01);
(Continued)

(58) Field of Classification Search
CPC ............ A61F 2/4225; A61F 2002/4233; A61F 2002/4235; A61F 2/4606
(Continued)

(56) References Cited

U.S. PATENT DOCUMENTS 5,021,056 A    6/1991  Hofmann
5,643,270 A *  7/1997  Combs ................... A61B 17/15
                                                       606/176

(Continued)

FOREIGN PATENT DOCUMENTS

WO    97-29704    8/1997

OTHER PUBLICATIONS

Greenhagen et al.—"Immediate Ambulation after a First Metatarsophalangeal Joint Fusion using a Locking Plate: Technique and case reports" Foot & Ankle Online Journal 3 (4). Apr. 2010.*

(Continued)

*Primary Examiner* — David H Willse
*Assistant Examiner* — Javier Blanco
(74) *Attorney, Agent, or Firm* — Heslin Rothenberg Farley & Mesiti P.C.

(57) ABSTRACT

Implant devices and cutting clamp apparatuses and methods for creating the implants for insertion into a patient's joint to restore anatomic length and assist in final positioning of the bones following removal of cartilage and/or bone in preparation for fusion. A first implant is a biplanar implant having a shape to mimic the normal anatomical shape of the bones the implant is configured to mate with. The first implant may be cut using a cutting clamp and jig having the anatomical shape of the bones the implant will be inserted within or between. A second implant is a cylindrical piece of bone having a convex end and a concave end for mating with bones reamed to have the opposite mating surfaces. The second implant is created using cup and cone reamers having dimensions corresponding to the size of the patient's bones. Surgical methods for inserting the implants within a patient.

2 Claims, 22 Drawing Sheets

Related U.S. Application Data

(60) Provisional application No. 61/473,194, filed on Apr. 8, 2011.

(51) Int. Cl.
*A61F 2/46* (2006.01)
*A61B 17/17* (2006.01)
*A61F 2/28* (2006.01)
*A61F 2/30* (2006.01)

(52) U.S. Cl.
CPC .......... *A61F 2/4606* (2013.01); *A61F 2/4644* (2013.01); *A61B 17/16* (2013.01); *A61B 17/1637* (2013.01); *A61B 17/1775* (2016.11); *A61B 2017/1775* (2013.01); *A61F 2002/2835* (2013.01); *A61F 2002/30622* (2013.01); *A61F 2002/4233* (2013.01); *A61F 2002/4235* (2013.01); *A61F 2002/4238* (2013.01); *A61F 2310/00011* (2013.01); *A61F 2310/00353* (2013.01)

(58) Field of Classification Search
USPC ....................................................... 623/21.19
See application file for complete search history.

(56) References Cited

U.S. PATENT DOCUMENTS

| | | | |
|---|---|---|---|
| 7,025,789 B2* | 4/2006 | Chow | A61F 2/4241 623/21.11 |
| 8,784,498 B2 | 7/2014 | Scheland | |
| 2002/0082604 A1 | 6/2002 | Abdelgany et al. | |
| 2002/0138078 A1 | 9/2002 | Chappuis | |
| 2007/0038303 A1 | 2/2007 | Myerson et al. | |
| 2009/0076513 A1* | 3/2009 | Szanto | A61B 17/1637 606/87 |
| 2011/0004255 A1* | 1/2011 | Weiner | A61B 17/1682 606/301 |

OTHER PUBLICATIONS

International Premlinary Report on Patentability for PCT/US2012/032765 dated Oct. 17, 2013.

International Search Report for PCT/US2012/032765 dated Oct. 25, 2012.

* cited by examiner

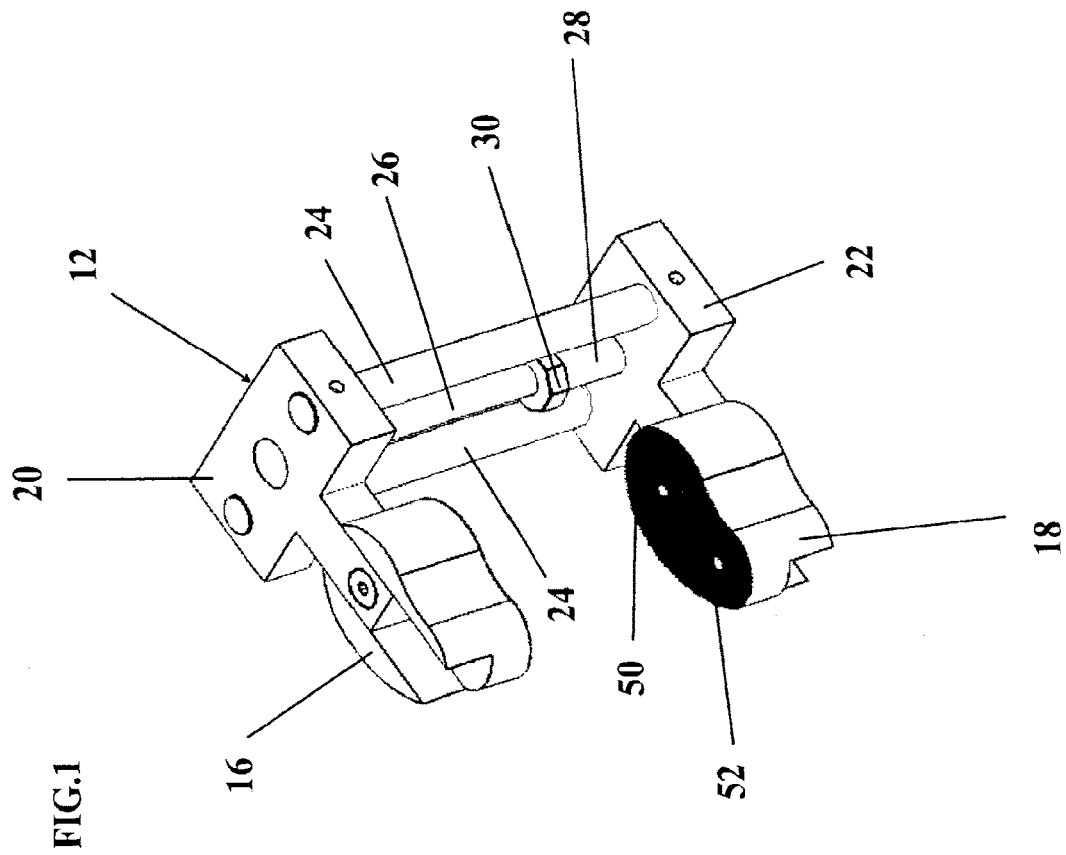
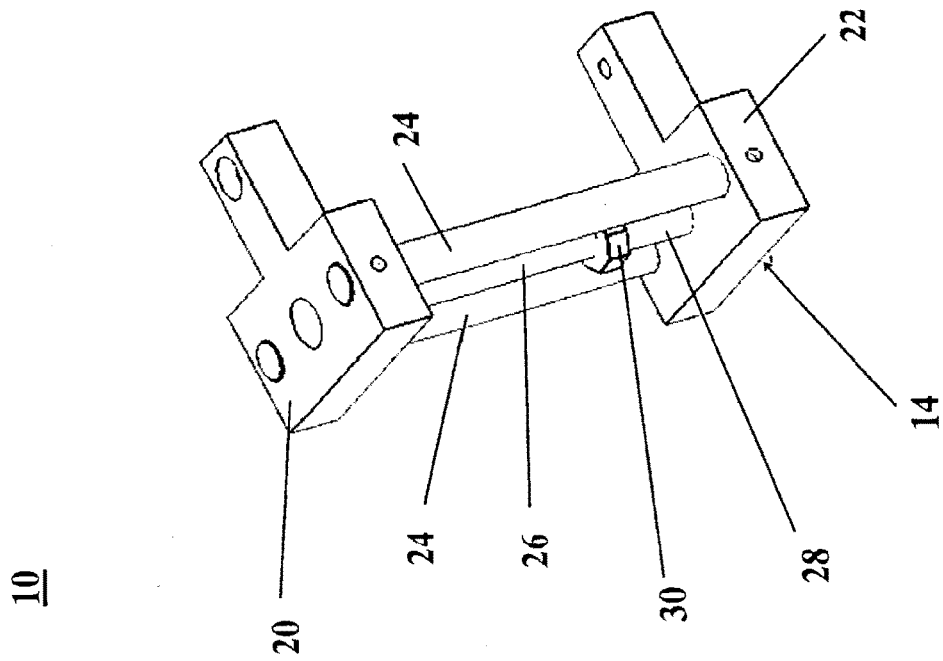
FIG.1

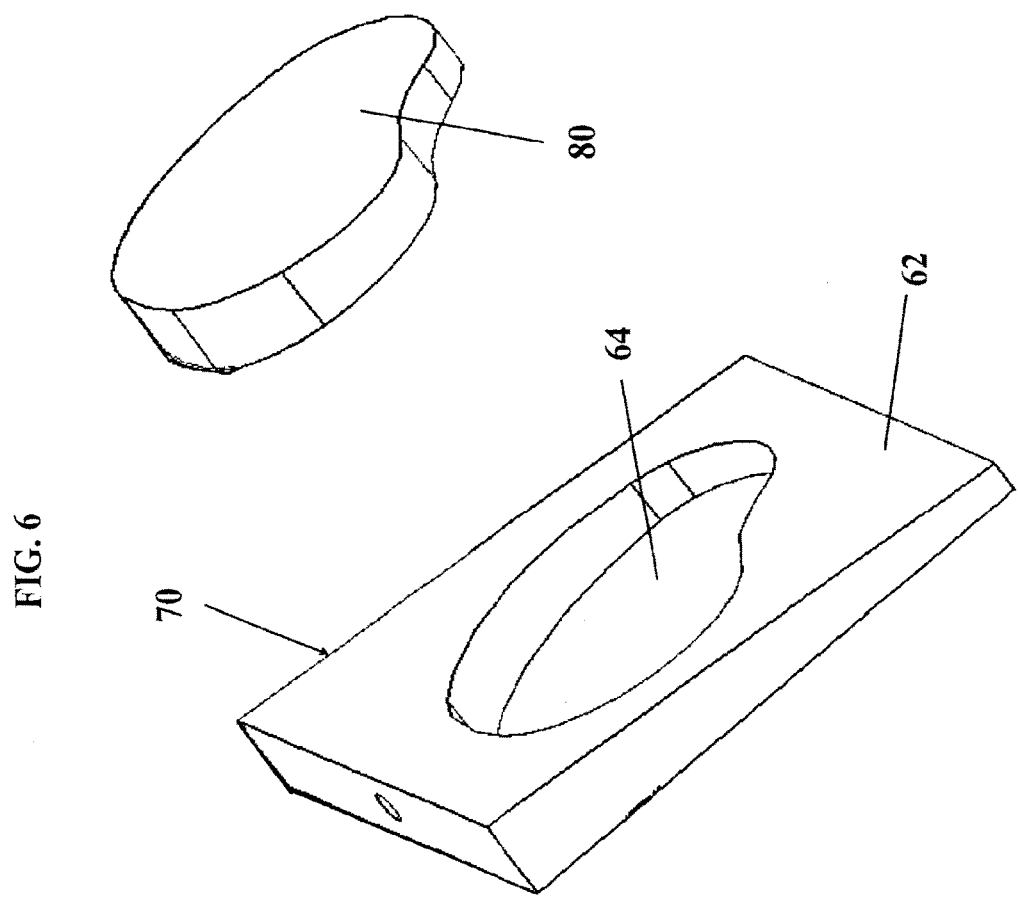

80

86   88

80

92   90

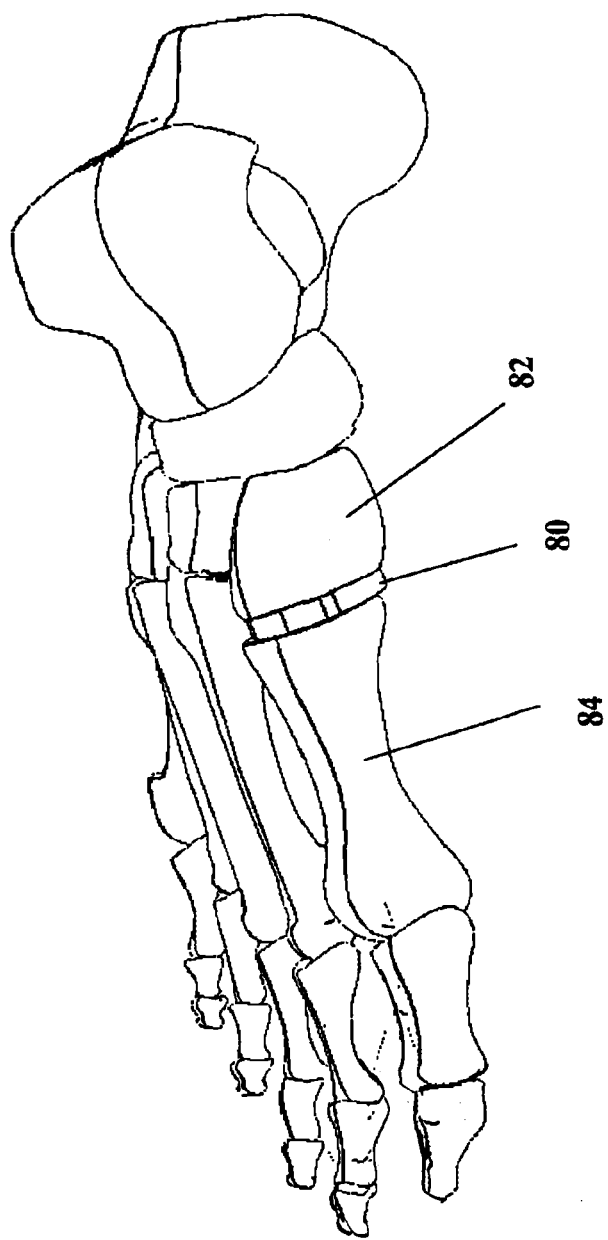

124

BONE IMPLANTS AND CUTTING
APPARATUSES AND METHODS

CROSS-REFERENCE TO RELATED
APPLICATION

This application is a divisional application of U.S. patent application Ser. No. 14/110,536, filed Oct. 8, 2013, which is a national stage filing under section 371 of International Application No. PCT/US2012/032765 filed on Apr. 9, 2012, and published in English on Oct. 11, 2012 as WO 2012/139114 and claims priority benefit under 35 U.S.C. §119(e) of U.S. provisional patent application No. 61/473,194 filed Apr. 8, 2011, which are each incorporated herein by reference in their entireties.

TECHNICAL FIELD

This present disclosure relates generally to the field of orthopaedics related to restoring anatomic length to joints between two bones in the upper and lower extremity following revision surgery, large deformities, injuries, and/or generally short anatomy.

BACKGROUND

The Lapidus procedure is commonly used to correct a hallux valgus deformity, which is a lateral deviation of the great toe, with subsequent hypermobility (or laxity). The Lapidus procedure is also commonly used to repair failed surgeries. Typically, a wedge of bone is removed in a biplanar direction at the distal end of the cuneiform, which will provide correction of the deformity and typically results in shortening of the great toe. The result of this shortening is a shift in weight distribution to the second ray, which can result in metatarsalgia. When the first ray is shortened the function of the patient's sesamoids may also be affected because of the change in weight distribution on the sesamoids. Currently to correct the shortening of the great toe when doing a Lapidus procedure, the accepted practice is for surgeons to make straight transverse cut on the metatarsal, then cut a wedge out of the cuneiform to obtain realignment of the intermetatarsal angle as determined by the surgeon, and insert a block of bone into the joint. The block of bone is then shaped by the surgeon until it fits within the joint. The shape of bone fails to help correct the angle. Blood supply to this joint can be limited in certain patients and using the overly processed bone makes it difficult to incorporate and heal which makes the bone prone to failure. It is well known that blood supply consideration to the joint and anatomical height and weight bearing through the joint are all concerns for healing the Lapidus procedure.

The metatarsal-phalangeal joint, when fused, is commonly denuded of cartilage by either using cup and cone reamers to minimize a loss of length and to provide versatility in final positioning or by making transverse type cuts using a saw blade. Generally, the cartilage surfaces of the metatarsal and proximal phalanx are removed and the end of the proximal phalanx is aligned with the end of the metatarsal with the two bones being fused together using screws, wires, or plates. In the case of revision surgeries of the metatarsal-phalangeal joint, the first ray may be shortened by 5-10+mm.

Accordingly, it is an object of the present invention to overcome one or more of the above-described drawbacks and/or disadvantages of the prior art. For example, in view of the deficiencies of the current implants and methods of performing the Lapidus procedure and fusion of the metatarsal-phalangeal joint, and similar implants and surgical methods for other areas of the body where multiple bone structures exist including, but not limited to, the hand, wrist and spine, it would be desirable to develop devices, instrumentation, and methods to allow a surgeon to achieve a satisfactory long term, predictable clinical outcome for these types of correction surgeries.

SUMMARY

The present invention is directed toward devices, instruments, and methods for cutting and inserting implants in the upper and lower extremity.

In one aspect of the present invention provided herein, is an implant for insertion into a patient's joint. This implant may be used for example during a Lapidus procedure. The implant having a body portion which is oblong. The implant is also tapered from the medial side to the lateral side of the implant as well as from the dorsal side to the plantar side of the implant. The implant may be made of metal, bone, polymer, or composite. For example, the implant may be made of titanium, cancellous bone, or polyetheretherketone.

In another embodiment of the present invention provided herein, is an implant device for replacing a joint. This implant may be used for example in the metatarsal-phalangeal joint. The implant device having a body portion with a cylindrical shape and a first end with a concave shape and a second end with a convex shape. The implant may be made of metal, bone, polymer, or composite, such as titanium, cancellous bone, or polyetheretherketone.

In another aspect of the present invention provided herein, is a surgical method for implanting an implant device into a joint, such as during a Lapidus procedure. The implant device having medial, lateral, dorsal, and plantar sides and wherein the implant device is tapered from the medial side to the lateral side and from the dorsal side to the plantar side creating a biplanar implant. The method including exposing the joint of a patient and preparing a first bone from a second bone to receive the implant then the implant is inserted between the first and second bones. The first and second bones may be prepared by denudation of the cartilage between the first and second bone. Once prepared the bone removed is determined and an appropriate size restoration wedge is selected and implanted. After the bone wedge is implanted, appropriate fixation is determined and applied. The method may also include fixing a fixation device, such as a plate, screws, wires, or external fixation to the first bone and second bone.

Yet another aspect of the present invention provided herein, is a surgical method for implanting an implant device having a concave end and a convex end into a joint, such an implant may be used in the metatarsal-phalangeal joint. The method includes exposing the joint of a patient and preparing a first bone from a second bone. The method further may include reaming the first bone and the second bone and inserting the implant device between the first bone and second bone. The method may also include fixing a fixation device to the first bone and second bone over the implant device. The first bone may be reamed to have a convex shape and the second end to have a concave shape. Alternatively, the first bone may be reamed to have a concave shape and the second bone to have a convex shape.

In a further aspect of the present invention provided herein, is a cutting clamp for cutting a length of bone for use in creating an implant. The cutting clamp may include a first clamp having attachment sites for top and bottom jaw members which are used to clamp a piece of bone during cutting of the general outline of the shape of the jaw members. The cutting clamp may further include a second clamp for attachment to the top and bottom jaw members on the side opposite the first clamp for cutting of the remaining general outline of the shape of the jaw members after removal of the first clamp to create a length of bone having a shape corresponding to the top and bottom jaw members.

In another aspect of the present invention provided herein, is a cutting jig for cutting an implantable device. The cutting jig includes a housing having an opening for inserting the length of bone cut by the cutting clamps and a screw for securing the length of bone to the cutting jig during cutting of the bone implant.

In yet another aspect of the present invention provided herein, is a method of cutting a length of bone for creating an implant. The method includes clamping a piece of bone between the top and bottom jaw members of a first clamp. Cutting a general outline of the shape of the jaw members into the piece of bone by tracing the exterior surface of the jaw members with a saw. Then the second clamp is attached to the jaw members and secures the piece of bone between the jaw members. The first clamp may then be removed and the second side of the piece of bone may be cut by tracing around the exterior surface of the jaw members with a saw. Once the entire general outline of the jaw members has been traced, the second clamp may be removed leaving a length of bone having the same shape as the jaw members. The method may further include obtaining a cutting jig to cut a bone implant from the length of bone. The length of bone is inserted into the opening of the cutting jig having a shape identical to the shape of the length of bone. Once the length of bone is inserted into the opening of the cutting jig, a screw may secure the length of bone to the cutting jig. Then the length of bone may be cut by running a saw along the planar surfaces of the cutting jig to create the bone implant having a desired angulation.

In still another embodiment of the present invention provided herein, is a method of cutting a length of bone to create an implant device. The method including shaping a length of bone into a cylinder and reaming a first end of the cylindrical bone. Then cutting the cylindrical bone to a desired length and reaming the second end of bone. The first end may be reamed to have a concave shape and the second end to have a convex shape or the first end may be reamed to have a convex shape and the second end to have a concave shape.

These and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 1 is an isometric view of a pair of bone clamps, in accordance with an aspect of the present invention;

FIG. 6 is an isometric view of one of the wedge shaped saw jigs of FIG. 5 and a bone wedge cut using the saw jig, in accordance with an aspect of the present invention;

FIG. 9 is a medial view of a right foot having the bone segment of FIGS. 7A-7E implanted in the foot, in accordance with an aspect of the present invention;

DETAILED DESCRIPTION FOR CARRYING OUT THE INVENTION

In this application, the words proximal, distal, anterior or plantar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the foot for brevity purposes, but it should be understood that the devices, instrumentation, and methods may be used with other bones of the body having similar structures, for example the upper extremity, and more specifically, with the bones of the wrist, hand, and arm.

Figure 2:
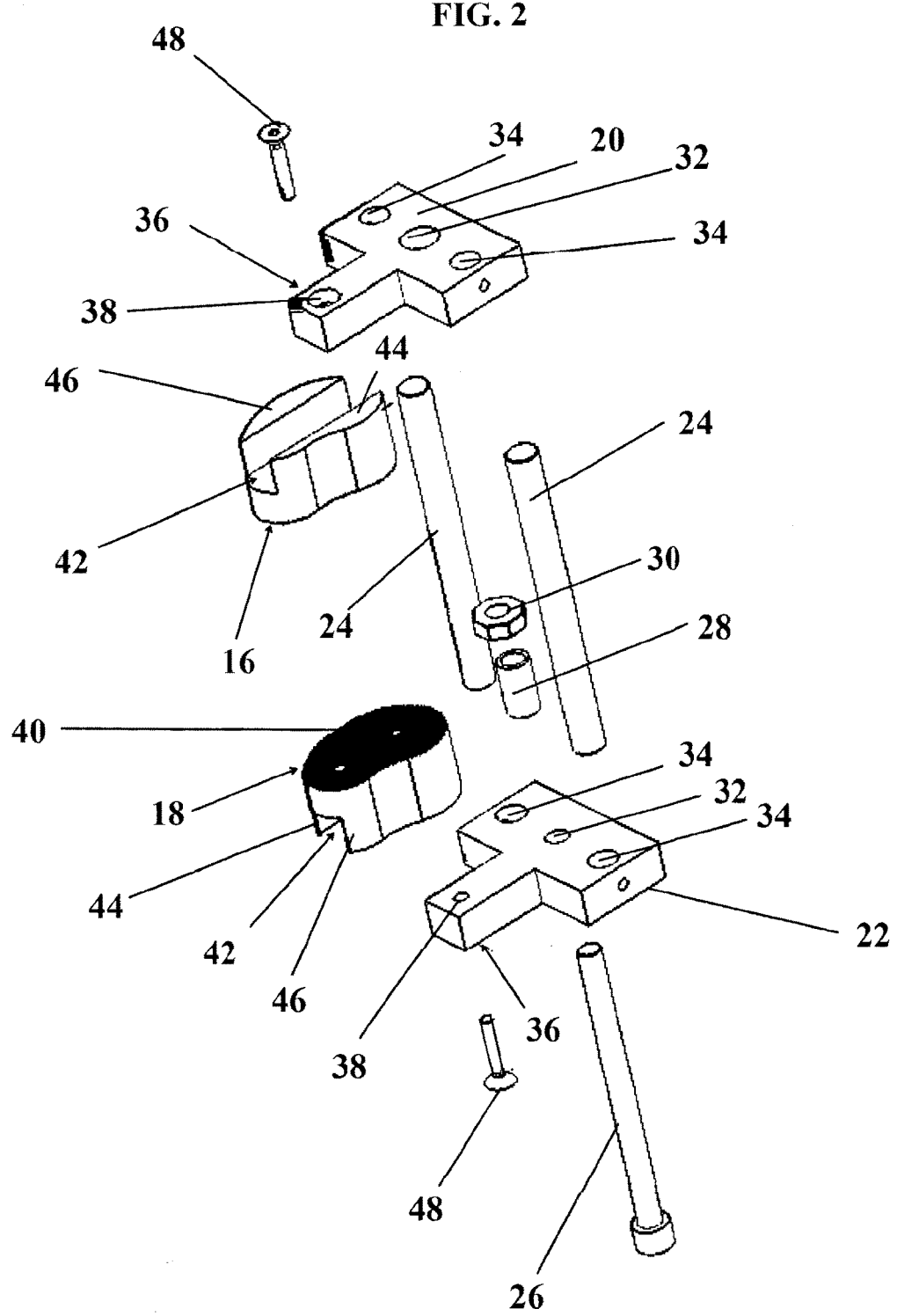
FIG. 2 is an exploded view of the bone clamps of FIG. 1, in accordance with an aspect of the present invention.
Figure 3:
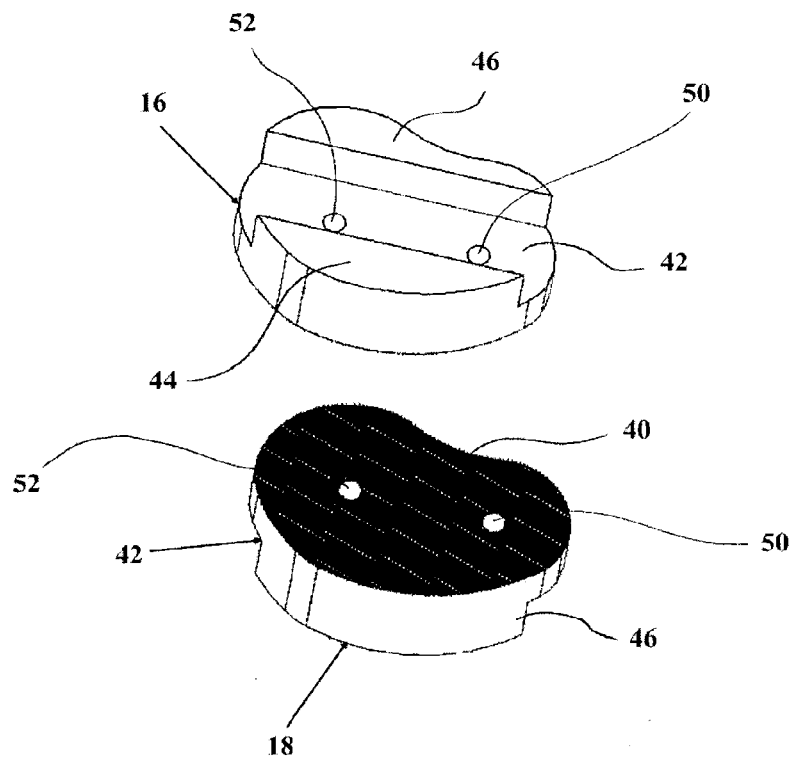
FIG. 3 is an isometric view of a mating pair of jaws for the bone clamp of FIG. 1, in accordance with an aspect of the present invention.

Referring to the drawings, wherein like reference numerals are used to indicate like or analogous components throughout the several views, and with particular reference to FIGS. 1-3, there is illustrated an exemplary embodiment bone clamping device 10 for cutting an allograft or xenograft bone into a specific shape for creating bone segments for implantation. The clamping device 10 having a first clamp 12, a second clamp 14, a first jaw 16, and a second jaw 18. As best illustrated in FIGS. 1 and 2, the first clamp 12 and the second clamp 14 both having a top base 20, a bottom base 22, two guide rails 24, a clamping screw 26, a spacer 28, and a retaining screw 30. The top base 20 having a first opening 32 for receiving the clamping screw 26, a pair of second openings 34 for receiving the two guide rails 24, and an attachment member 36 having a third opening 38 for attaching the first jaw 16. The bottom base 22 having a first opening 32 for receiving the clamping screw 26, a pair of second openings 34 for receiving the two guide rails 24, and an attachment member 36 having a third opening 38 for attaching the second jaw 18.

Figure 4:
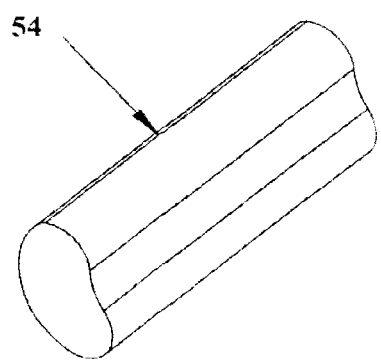
FIG. 4 is an isometric view of a piece of bone cut using the bone clamps of FIG. 1, in accordance with an aspect of the present invention.

The first jaw 16 and the second jaw 18 have an outer anatomical profile designed to guide a cutting device, such as a saw blade, for cutting a allograft or xenograft bone into a shaft of bone 54 (See FIG. 4). As depicted in FIGS. 1-3, the first jaw 16 and second jaw 18 are shaped for cutting allograft or xenograft bone for creating Lapidus implants for insertion at the tarsal-metatarsal joints, as well as for insertion into other joints in the upper and lower extremity having similar shapes. The clamping device 10 may also be used for cutting other bones having various sizes and shapes by replacing the first jaw 16 and second jaw 18 with differently shaped jaw members. For example, the clamping device 10 may also be used for creating implants for insertion between the cuboid and calcaneous, within the calcaneous, and at the subtalar joint, as well as in the upper extremity at the metacarpo-phalangeal joint, carpo-metacarpal joint and at other joints or bones within the human body. The first jaw 16 and second jaw 18 may have opposing serrated faces 40 for clamping the allograft or xenograft bone during cutting. As best illustrated in FIG. 3, the first jaw 16 and second jaw 18 may also have a channel 42 in the back side of the first jaw 16 and second jaw 18 and having a first side member 44 and a second side member 46 for securing the first jaw 16 and second jaw 18 to the attachment members 36 of the top base 20 and bottom base 22. The first jaw 16 and second jaw 18 having a first opening 50 and a second opening 52 which may be used to secure the first jaw 16 and second jaw 18 to the attachment members 36.

As best illustrated in FIGS. 1 and 2, the first jaw 16 is secured to the attachment member 36 of the top base 20 by a fastener 48, such as a screw, and the second jaw 18 is secured to the attachment member 36 of the bottom base 22 by a fastener 48. The fasteners 48 pass through the third opening 38 in the attachment members 36 and into the first openings 50 in the first jaw 16 and second jaw 18 to secure the first jaw 16 and second jaw 18 to the attachment members 36. A piece of allograft or xenograft bone, (Not Shown), may then be positioned on the second jaw 18 of the bottom base 22 for cutting. The piece of allograft or xenograft bone may preferably be a square, cylinder, or any shape having at least two parallel surfaces for being clamped between the first jaw 16 and the second jaw 18. The top base 20 may then be lowered along the two guide rails 24 until the first jaw 16 contacts the top of the allograft or xenograft bone. Once the first jaw 16 and second jaw 18 are in contact with the allograft or xenograft bone and the allograft or xenograft bone is positioned for cutting, the clamping screw 26 may be tightened securing the allograft or xenograft bone in place in the first clamp 12. The spacer 28 and retaining screw 30 may also be used to secure the first clamp 12 before cutting the allograft or xenograft bone. Once the allograft or xenograft bone is captured between the first jaw 16 and second jaw 18 of the first clamp 12, a cutting device, such as a saw blade, preferably long enough to contact the first jaw 16 and the second jaw 18 simultaneously, may trace around the outer profile of the first jaw 16 and second jaw 18. After the saw blade traces around the outer profile with the first clamp 12 attached, the second clamp 14 may be secured to the second jaw 18 at second opening 52 using a fastener 48 as described above. Then the top base 20 may be slid into place in the first jaw 16, secured using clamping screw 26 of the second clamp 14. A fastener 48 may be used to attach the attachment member 36 of the top base 20 to the first jaw 16 at second opening 52. The first clamp 12 may then be loosened and removed from the allograft or xenograft bone. Once the first clamp 12 is removed the user may then use a saw blade to trace around the outer profile of the uncut portion of the bone along the first jaw 16 and the second jaw 18. Once the second cut is complete, a shaft of bone 54 with a profile matching that of the first jaw 16 and second jaw 18 is created, as best seen in FIG. 4. As illustrated in FIG. 4, the shaft of bone 54 may have a shape which corresponds to the shape of the tarsal-metatarsal joints, which may appear to have an oblong shape, more particularly a kidney bean shape or the shape of any other target location in which the implant may be placed.

Figure 5A:
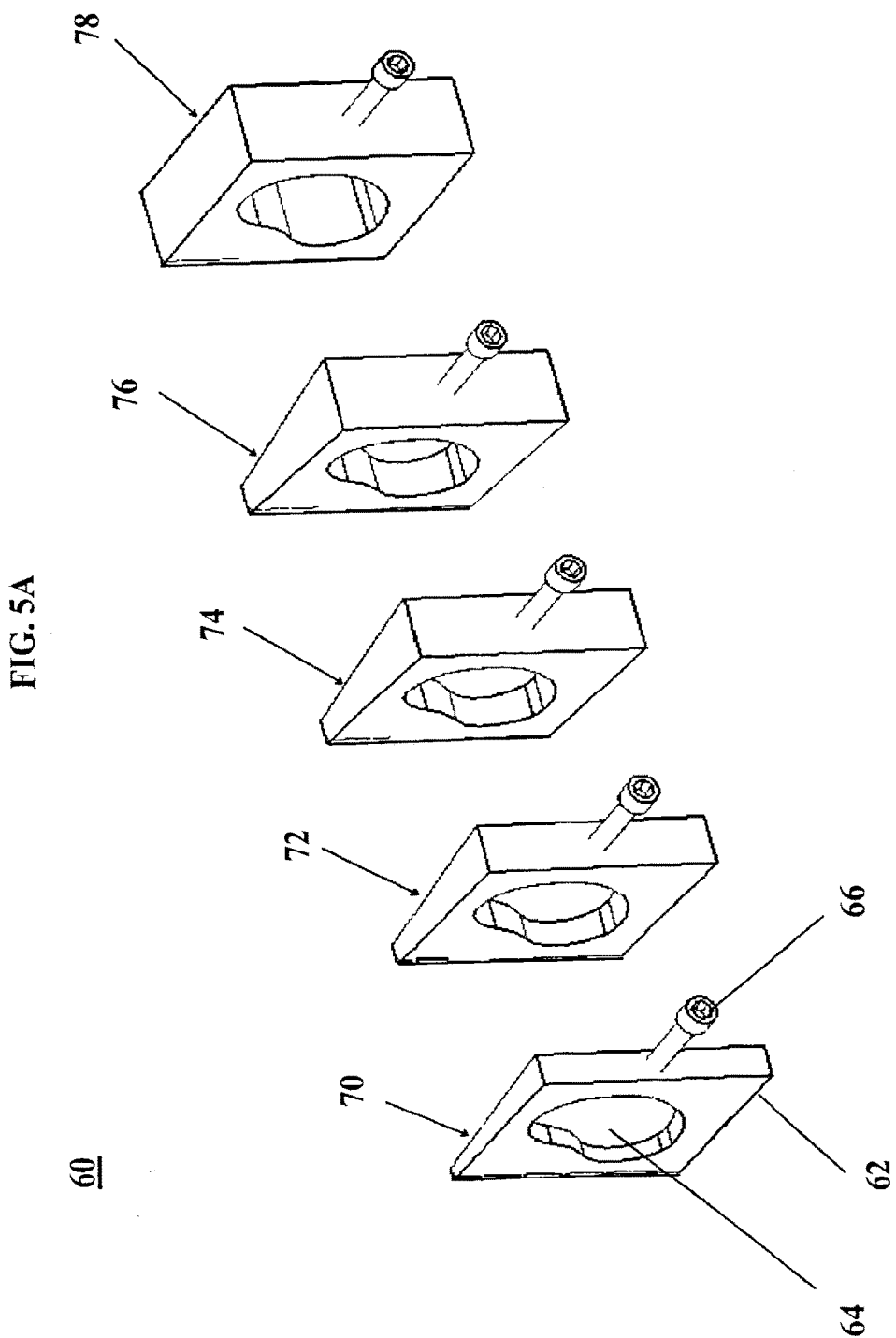
FIG. 5A is an isometric view of a set of wedge shaped saw jigs, in accordance with an aspect of the present invention.
Figure 5B:
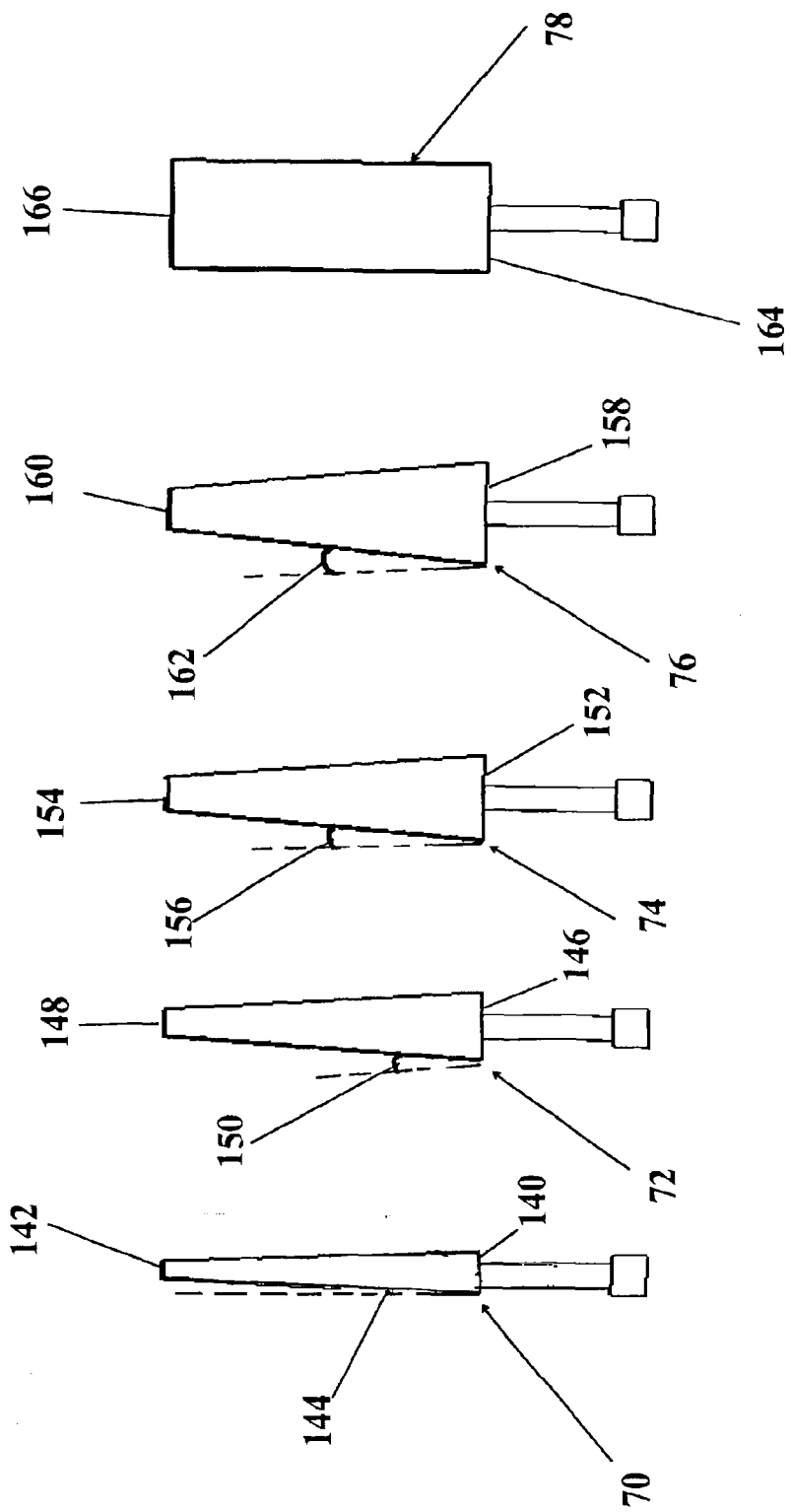
FIG. 5B is a top view of the set of wedge shaped saw jigs of FIG. 5A, in accordance with an aspect of the present invention.

As best seen in FIG. 5A, is a set of saw jigs 60 for creating bone wedges of various sizes. The saw jigs 60 having a plate 62 with an oblong shaped opening 64, more preferably Lapidus shaped as depicted, and a locking screw 66. The saw jigs 60 may be created in various sizes for example preferably ranging from about 3 mm and 3° to about 20 mm to 20° to correspond to various degrees of correction, as well as for example 5 mm and 0° to about 20 mm and 0°. The saw jigs 60 may more preferably range from about 5 mm and 5° to about 12 mm and 12° to correspond to the various degrees of correction, as well as for example 14 mm and 0° to other thicknesses and angulations which may be cut to a final size during a case intra-operatively. Other sizes are also contemplated which correspond to the patient's anatomy as well as other sizes with no angles which may be sized intra-operatively. The saw jigs 60 include a first saw jig 70, a second saw jig 72, a third saw jig 74, a fourth saw jig 76, and a fifth saw jig 78, as depicted in the embodiment in FIGS. 5A-5B. The first saw jig 70 having a first end 140, a second end 142, and an angle 144 where for example the first end 140 is about 5 mm and the angle 144 is about 5°. The second saw jig 72 has a first end 146, a second end 148, and an angle 150 where for example the first end 146 is about 8 mm and the angle is about 8°. The third saw jig 74 has a first end 152, a second end 154, and an angle 156 where the first end 152 is about 10 mm and the angle is about 10°. The fourth saw jig 76 has a first end 158, a second end 160, and an angle 162 where for example the first end 158 is about 12 mm and the angle 162 is about 12°. The fifth saw jig 78 has a first end 164 and a second end 166 with a uniform thickness where for example the first end 164 and second end 166 are about 14 mm. The saw jigs 60 wherein where the first ends 140, 146, 152, 158, and 164 are opposite the second ends 142, 148, 154, 160, and 166. The shaft of bone 54 which was cut using the clamping device 10, as seen in FIG. 4, would be inserted into the opening 64 of one of the set of saw jigs 60 having the desired dimensions for implantation and the shaft of bone 54 would be secured using the locking screw 66. Then a band saw blade or other cutting device, not shown, could be operated along both sides of the saw jig selected from the set of saw jigs 60 creating a bone wedge 80. The bone wedge 80 may be cut using the saw jigs 60 to mimic the anatomical considerations of the bones the bone wedge 80 is being inserted between with the desired angular corrections for a given procedure.

Figure 7A:
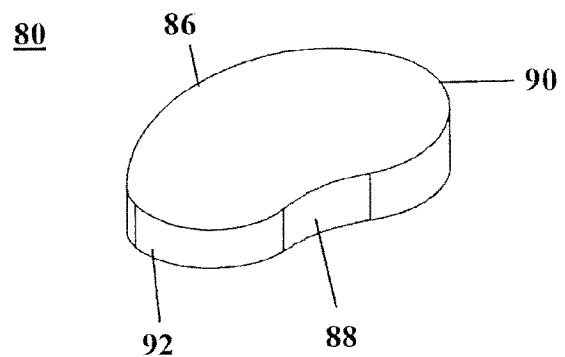
FIG. 7A is an isometric view of a wedge shaped bone segment with an anatomical profile, in accordance with an aspect of the present invention.
Figure 7B:
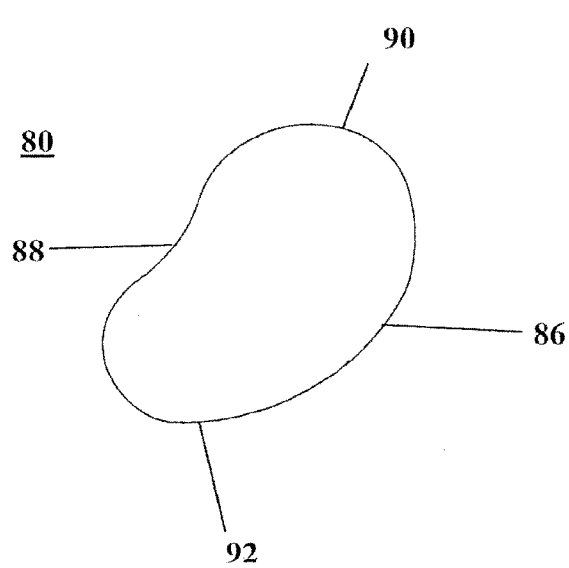
FIG. 7B is a distal side view of the wedge shaped bone segment of FIG. 7A, in accordance with an aspect of the present invention.
Figure 7C:
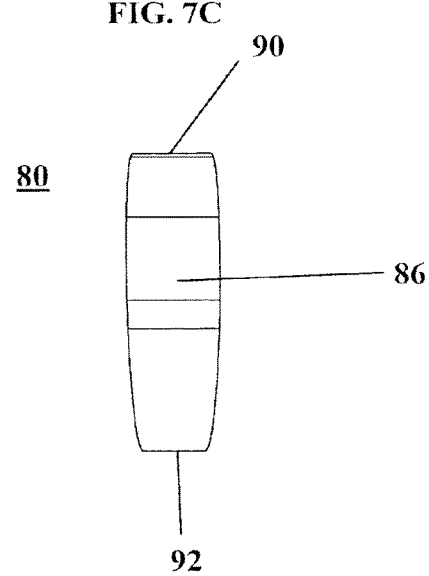
FIG. 7C is a medial side view of the wedge shaped bone segment of FIGS. 7A-7B, in accordance with an aspect of the present invention.
Figure 7D:
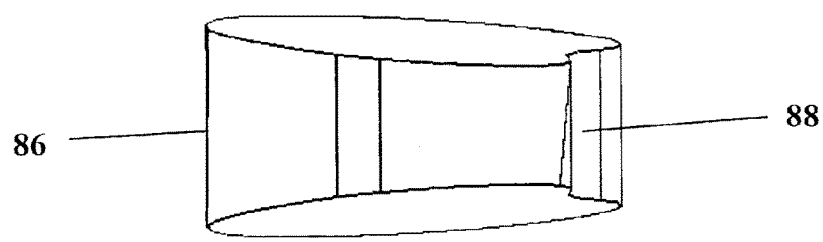
FIG. 7D is a plantar side view of the wedge shaped bone segment of FIGS. 7A-7C, in accordance with an aspect of the present invention.
Figure 7E:
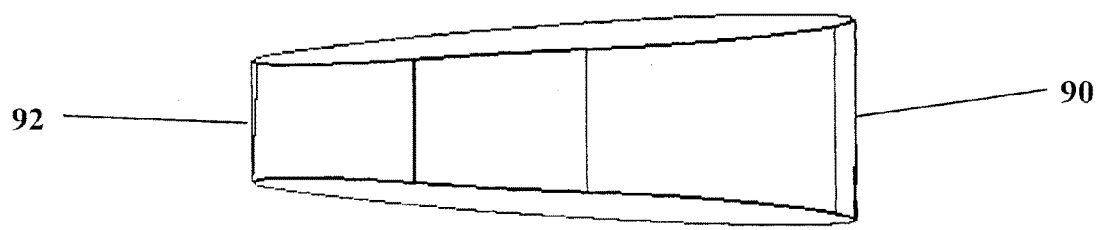
FIG. 7E is a lateral side view of the wedge shaped bone segment of FIGS. 7A-7D, in accordance with an aspect of the present invention.
Figure 8:
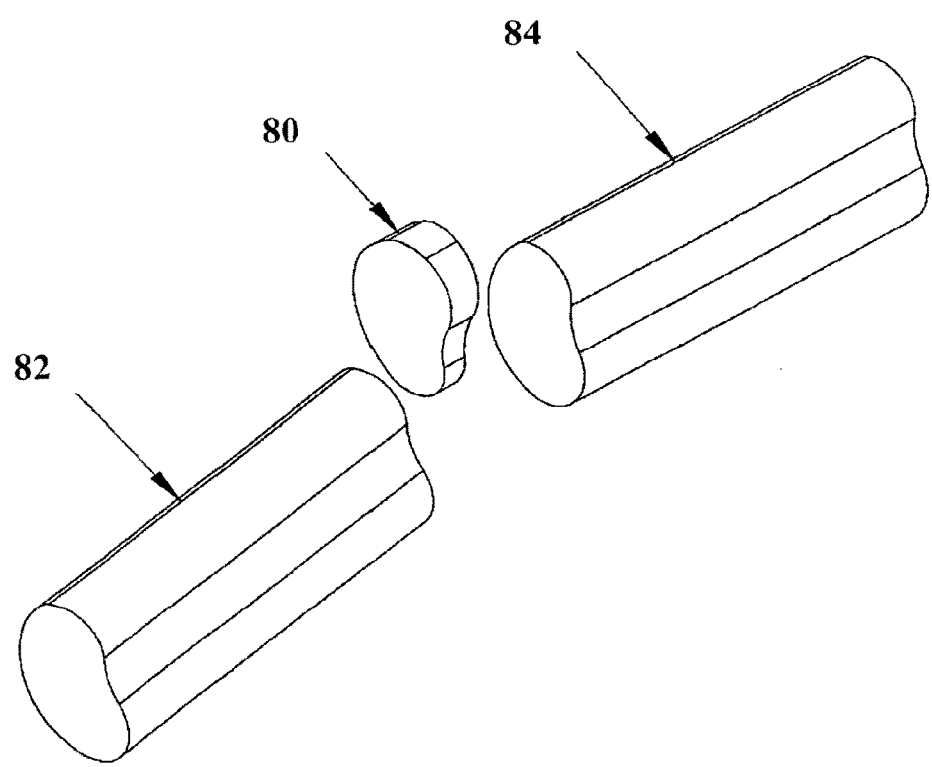
FIG. 8 is an isometric view of two prepared bone surfaces and the wedge shaped bone segment of FIGS. 7A-7E with an anatomical profile, in accordance with an aspect of the present invention.

Referring now to FIGS. 6-9, an example of the bone wedge 80 which may be cut from the first saw jig 70 is shown. The bone wedge 80 has a profile identical to the Lapidus shaped opening 64 of the first saw jig 70. Illustrated in FIGS. 7A-7E, are an isometric view, a distal side view, a medial side view, a plantar side view, and a lateral side view of the bone wedge 80, respectively. The bone wedge 80 is cut to a desired restoration length necessary for the patient receiving the implant and has an outer anatomical profile that mimics the anatomical considerations of the bones it is being inserted between. For example, as depicted in FIGS. 8 and 9, the outer anatomical profile of the bone wedge 80 on the proximal and distal sides is cut to mimic the shapes of the medial cuneiform 82 and metatarsal 84 bones, which is an oblong shape, or more preferably is a kidney shape. In addition, the bone wedge 80 is cut with a desired angle thereby creating a desired angular offset between the medial cuneiform 82 and the metatarsal 84. The bone wedge 80 may be cut in the saw jigs 70, 72, 74, or 76 to create a wedge geometry having reproducible angular corrections which are desired for a given procedure. For example, in the Lapidus implant the desired angulation may be used to correct valgus and plantar angulation of the bones by tapering the bone wedge 80 from the medial side to the lateral side and from the dorsal side to the plantar side. The bone wedge 80 may have heights ranging from about 25 mm to 40 mm, width ranging from about 10 mm to 30 mm, and thickness ranging from about 0 mm to 20 mm at the dorsal side and the medial side and tapering from the dorsal side to plantar side and medial side to lateral side at an angle ranging from about 0° to 20°. More preferably, the bone wedges 80 have heights of about 32 mm, a width of about 21 mm at the dorsal medial corner, and functional thickness of 5 mm and 5°, 8 mm and 8°, 10 mm and 10°, 12 mm and 12°, and 14 mm and 0°. It is also contemplated that the taper of the thickness of the bone wedge 80 may be from the dorsal-medial corner to the plantar-lateral corner.

As seen in FIGS. 7D-7E, the bone wedge 80 is tapered in the medial-lateral plane from the medial side 86 of the bone wedge 80 to the lateral side 88 and in the dorsal-planatar plane from the dorsal side 90 of the bone wedge 80 to the plantar side 92. More particularly, the bone wedge 80 may be tapered from the dorsal-medial corner to plantar-lateral corner of the Z-axis. Thus, a bi-planar surface is created on the bone wedge 80 wherein the proximal surface converges towards the distal surface. The bone wedge 80 may be cut from bone for example cancellous bone and/or a combination of cortical or cancellous bone, or may be made of metal, for example a titanium material, or may be made of a polymer or composite, for example a polyetheretherketone ("PEEK") material, or other material appropriate for implantation. In the event allograft or xenograft bone is used it may be minimally processed allograft or xenograft bone having stout cancellous or cancellous and cortical bone and is used for retaining maximum osteoinductivity. The minimally processed allograft or xenograft bone is not gamma irradiated to preserve mechanical integrity and is not exposed to peroxides to preserve osteoinductivity.

A surgical method for implanting the bone wedge 80 into a joint, shown in FIG. 23, will now be described. The method utilizes some of the devices, instruments, features, aspects, components and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

Assuming the patient has a hallux valgus deformity which needs to be corrected, an implant device, such as bone wedge 80, and fixation members, such as pins, screws, plates, or external fixation may be used to correct the deformity. For example, the hallux may be pointing outward away from the midline of the body and need to be realigned, wherein the first metatarsal and phalanx may be angled away from the midline of the body and towards the other toes. As the first metatarsal and medial cuneiform are being used for exemplary purposes only, the generic term "first bone" may be used hereinafter to refer to the first metatarsal bone, or any other bone that includes similar features, positioning, orientation, function or the like. Similarly, the generic term "second bone" may be used hereinafter to refer to the medial cuneiform, or any other bone that includes similar features, positioning, orientation, function or the like. Likewise, the generic term "first joint" may be used hereinafter to refer to the joint between the first metatarsal and the medial cuneiform, or any other joint that includes similar features, positioning, orientation, function or the like.

Figure 23:
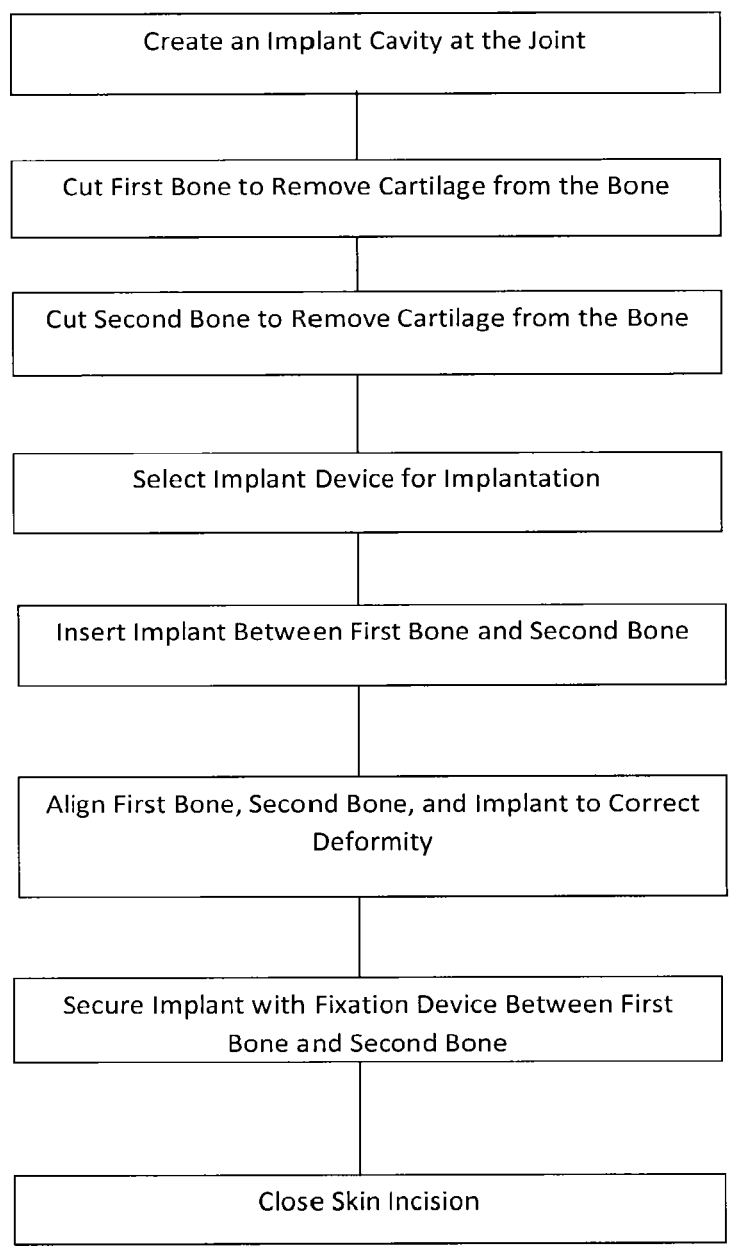
FIG. 23 depicts one embodiment of a surgical method for implanting an implant device into a patient's body, in accordance with an aspect of the present invention.

As illustrated in FIG. 23, in order to correct the deformity in the first and second bones, an implant cavity will first be formed at the first joint, whereby the first joint is exposed so the first and second bones may be prepared for the arthrodesis. The first bone will then be cut to remove the cartilage from the base of the first bone. Next, the second bone will be cut to remove the cartilage from the distal aspect of the second bone. The cut to the second bone should be performed at a 45° angle dorsal medial to plantar lateral to provide two planes of correction to the first and second bones. Once the first and second bone have been prepared the surgeon may either select a bone wedge 80 from a kit containing a set of various sizes of bone wedges and implant the bone wedge 80 having the desired width and angle. Alternatively, if a different size bone wedge is needed the surgeon may select the bone wedge 80 from the kit having a uniform size and cut a custom bone wedge, (Not Shown), for the desired site intra-operatively. Once a bone wedge 80 has been selected it may then be inserted between the first and second bones and aligned to correct the deformity of the bones. After the correct alignment has been achieved the bone wedge 80 must be fixed within the first joint with one or more fixation devices. The fixation devices may include screws, wires, plates, or external fixation. Once the bone wedge 80 is secured within the first joint the skin incision may be closed up by the surgeon.

One advantage of the embodiments discussed herein of the present invention is that the bone wedge 80 enables correction in both the dorsal-plantar plane and medial-lateral plane. Alternatively and more specifically, the bone wedge 80 may provide angulation from the dorsal-medial plane to the plantar-lateral plane. In addition, the Lapidus procedure allows for plantar angulation of the first ray to restore weight distribution back to the sesamoids. The custom allograft bone wedge 80 is designed to mimic the oblong shape of the joint, more particularly the kidney bean shape of the joint, and restore the angulation of the wedge to 45 degrees from the z-axis to provide both plantar and valgus angulation of the proximal phalanx. Another advantage of the embodiments of the present invention discussed herein is that the bone wedge 80 may be composed of the most robust cancellous or cancellous and cortical structure and will preserve the structure and osteoinductivity of the adjacent bones. A further advantage of the present invention discussed herein is that the bone wedge 80 may be used to correct a number of deformities in various joints and bones of the upper and lower extremities.

Figure 10A:
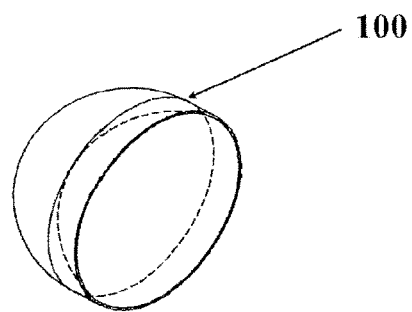
FIG. 10A is an isometric view of a restoration bone segment, in accordance with an aspect of the present invention.
Figure 10B:
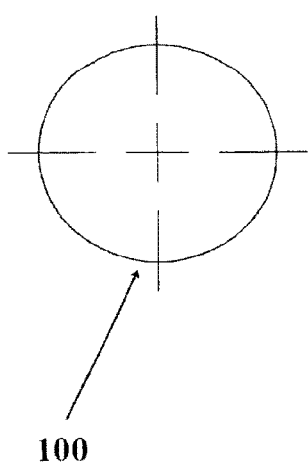
FIG. 10B is a front view of a restoration bone segment, in accordance with an aspect of the present invention.
Figure 10C:
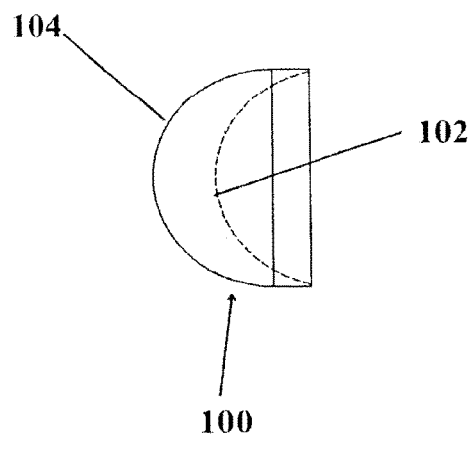
FIG. 10C is a side view of a restoration bone segment, in accordance with an aspect of the present invention.
Figure 11:
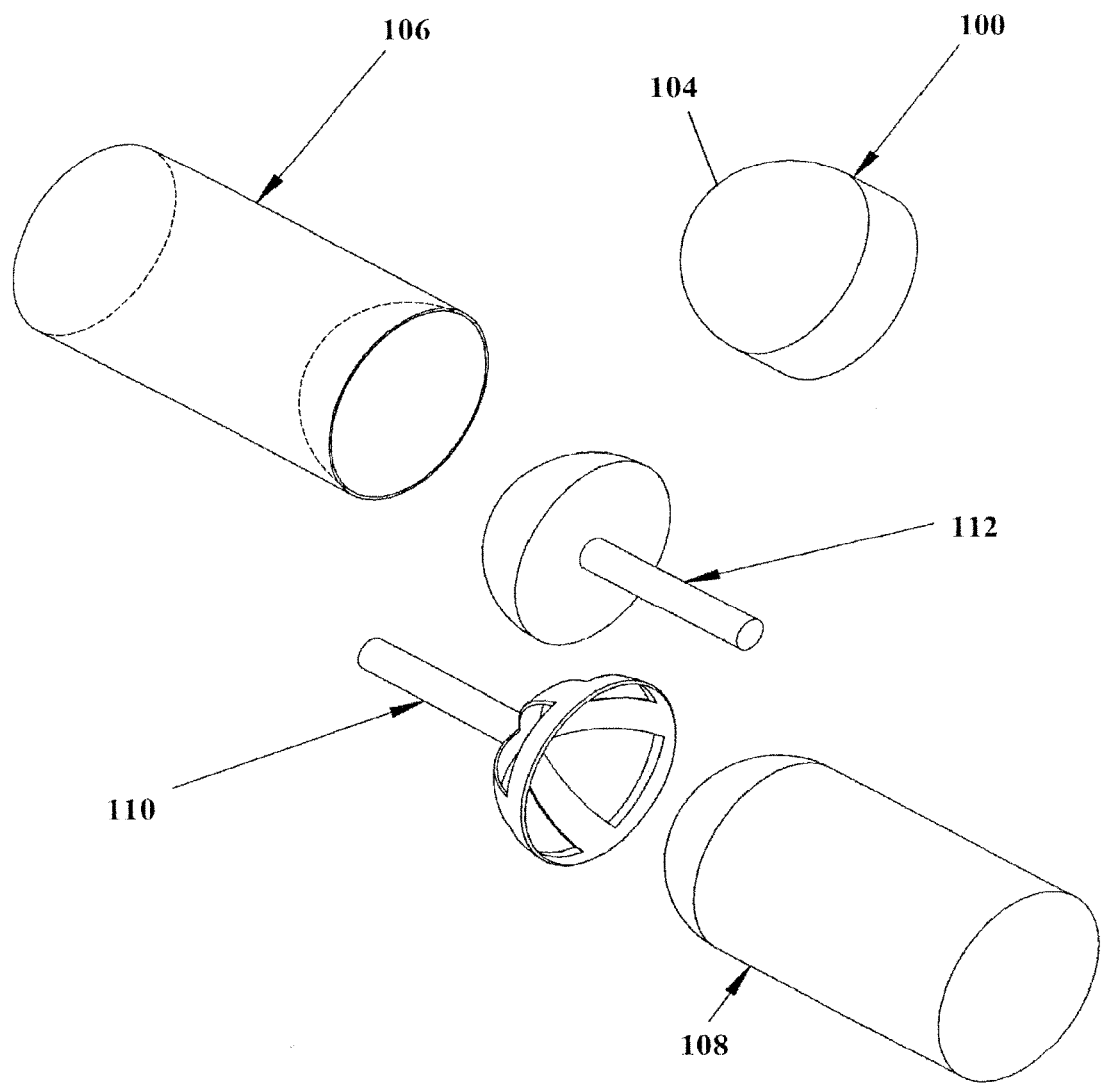
FIG. 11 is an isometric view of a cup and cone reamers, two prepared bone surfaces, and a restoration bone segment of FIGS. 10A-10C, in accordance with an aspect of the present invention.

Referring now to FIGS. 10A-21, illustrated in these figures are various implants and surgical instruments including cup and cone reamers and a restoration bone segment. Best seen in FIGS. 10A-10C, is a restoration bone segment 100 which may be used for insertion between two bone segments to adjust their overall length. The restoration bone segment 100 may be cut from bone, for example cancellous bone or combination cancellous/cortical bone, may be made of metal, for example a titanium material, or may be made of a polymer or composite, for example a polyetheretherketone ("PEEK") material. The allograft or xenograft bone is a minimally processed allograft or xenograft bone having stout cancellous bone or cancellous and cortical bone and is used to maintain maximum osteoinductivity. The restoration bone segment 100 has a concave end 102 for mating with a convex bone 108 and a convex end 104 for mating with a concave bone 106, as depicted in FIG. 11. The restoration bone segment 100 may be made using a cone reamer 110 and a cup reamer 112 which creates a ball and socket like configuration. To create the restoration bone segment 100, a cylindrical piece of bone having the desired circumference may have a convex end 104 created using the cone reamer 110, then the bone may be cut to the desired length and the cup reamer 112 may be used to create the concave end 102. Alternatively, the piece of bone may have the concave end 102 created using the cup reamer 112, then the bone may be cut to the desired length and the cone reamer 110 used to create the convex end 104. In addition, the cone reamer 110 and cup reamer 112 may be used to prepare the bones for insertion of the restoration bone segment 100, described in greater detail hereinafter.

Figure 12:
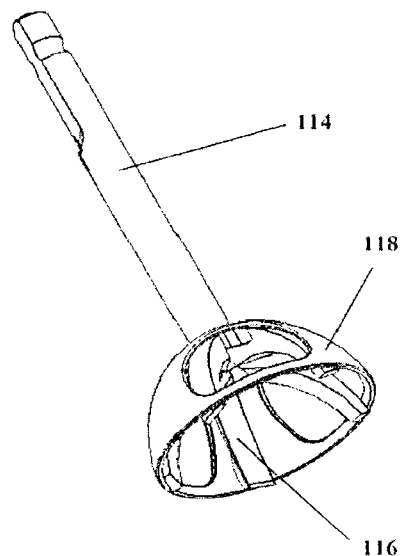
FIG. 12 is an isometric view of another embodiment of a cup reamer and cover, in accordance with an aspect of the present invention.
Figure 13:
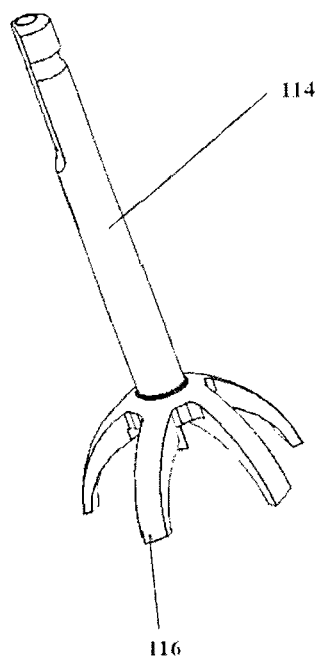
FIG. 13 is an isometric top view of the cup reamer of FIG. 12, in accordance with an aspect of the present invention.
Figure 14:
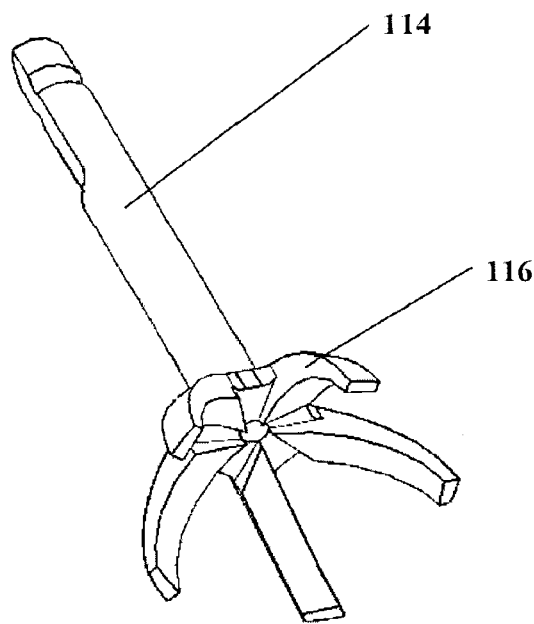
FIG. 14 is an isometric bottom view of the cup reamer of FIG. 12, in accordance with an aspect of the present invention.
Figure 15:
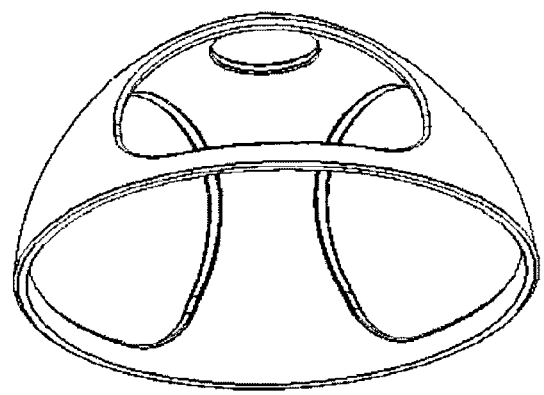
FIG. 15 is an isometric view of the cup reamer cover of FIG. 12, in accordance with an aspect of the present invention.

Another embodiment of the cone reamer 110 is depicted in FIG. 12. The cone reamer 110 has a shank 114 for insertion into a drill, a cutting edge 116 for cutting a convex shape into bone, and a backstop 118 to protect the opposite side from damage during reaming. As illustrated in FIGS. 13 and 14, it is also contemplated that the cone reamer 110 may be used without the backstop 118, seen in FIG. 15. Various size cutting edges 116 may be provided based on the desired diameter of the convex end 104 of the bone segment 100 and corresponding convex bone 108. The inner diameter of the cutting edge 116 corresponds to the outer diameter of the bone cut with the cone reamer 110.

Figure 16A:
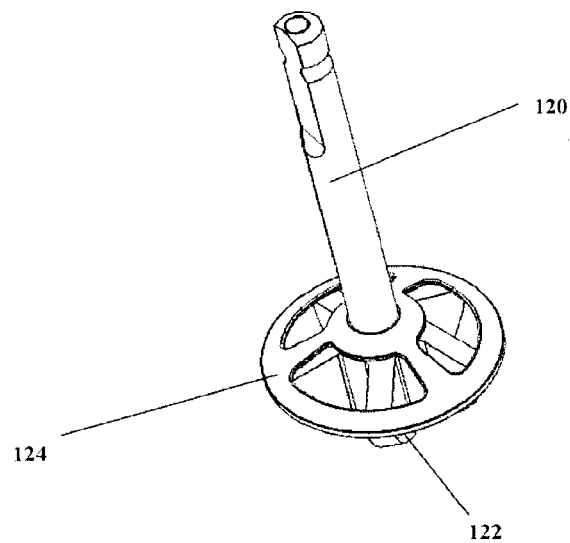
FIG. 16A is an isometric top view of another embodiment of a cone reamer and cover, in accordance with an aspect of the present invention.
Figure 16B:
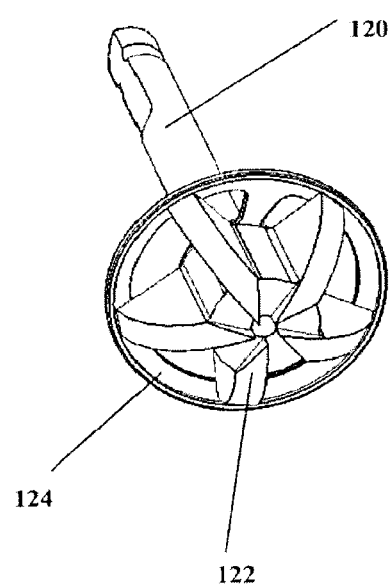
FIG. 16B is an isometric bottom view of the cone reamer and cover of FIG. 16A, in accordance with an aspect of the present invention.
Figure 17:
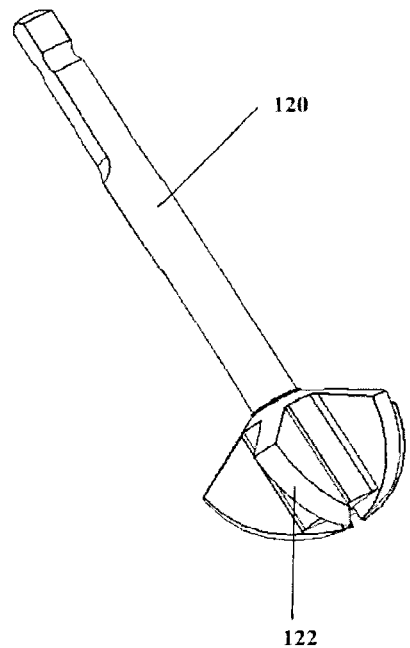
FIG. 17 is an isometric side view of the cone reamer of FIGS. 16A and 16B, in accordance with an aspect of the present invention.
Figure 18:
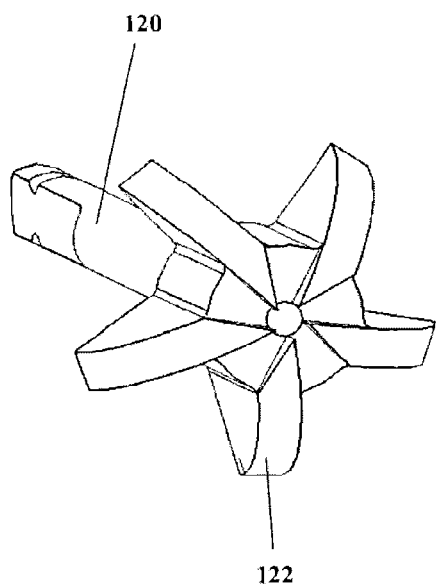
FIG. 18 is an isometric bottom view of the cone reamer of FIG. 17, in accordance with an aspect of the present invention.
Figure 19:
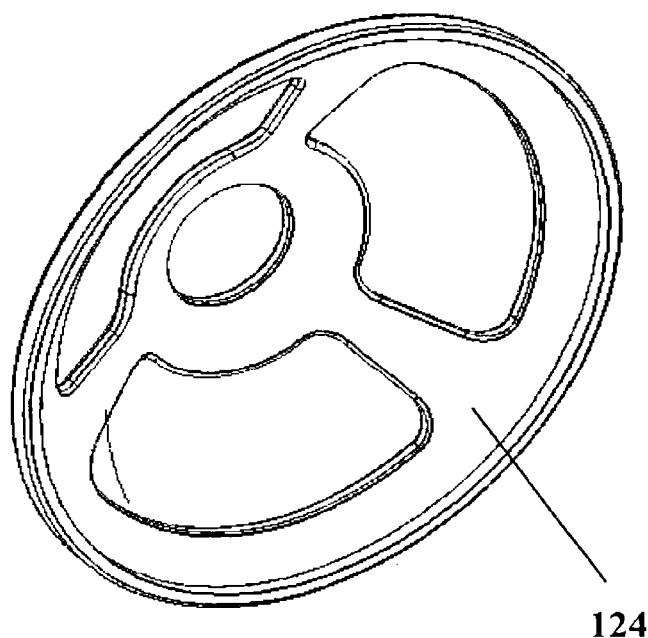
FIG. 19 is an isometric bottom view of the cone reamer cover of FIGS. 16A and 16B, in accordance with an aspect of the present invention.

Illustrated in FIGS. 16A-16B is another embodiment of the cup reamer 112. The cup reamer 112 has a shank 120 for insertion into a drill, a cutting edge 122 for cutting a concave shape into a bone, and a backstop 124 to protect the opposite side from damage during reaming. It is also contemplated and depicted in FIGS. 17-18 that the cup reamer 112 may be used without the backstop 124, seen in FIG. 19. Various size cutting edges 122 may be provided based on the desired diameter of the concave end 102 of the bone segment 100 and corresponding concave bone 106. The outer diameter of the cutting edge 122 corresponds to the inner diameter of the bone cut with the cup reamer 112.

Figure 20:
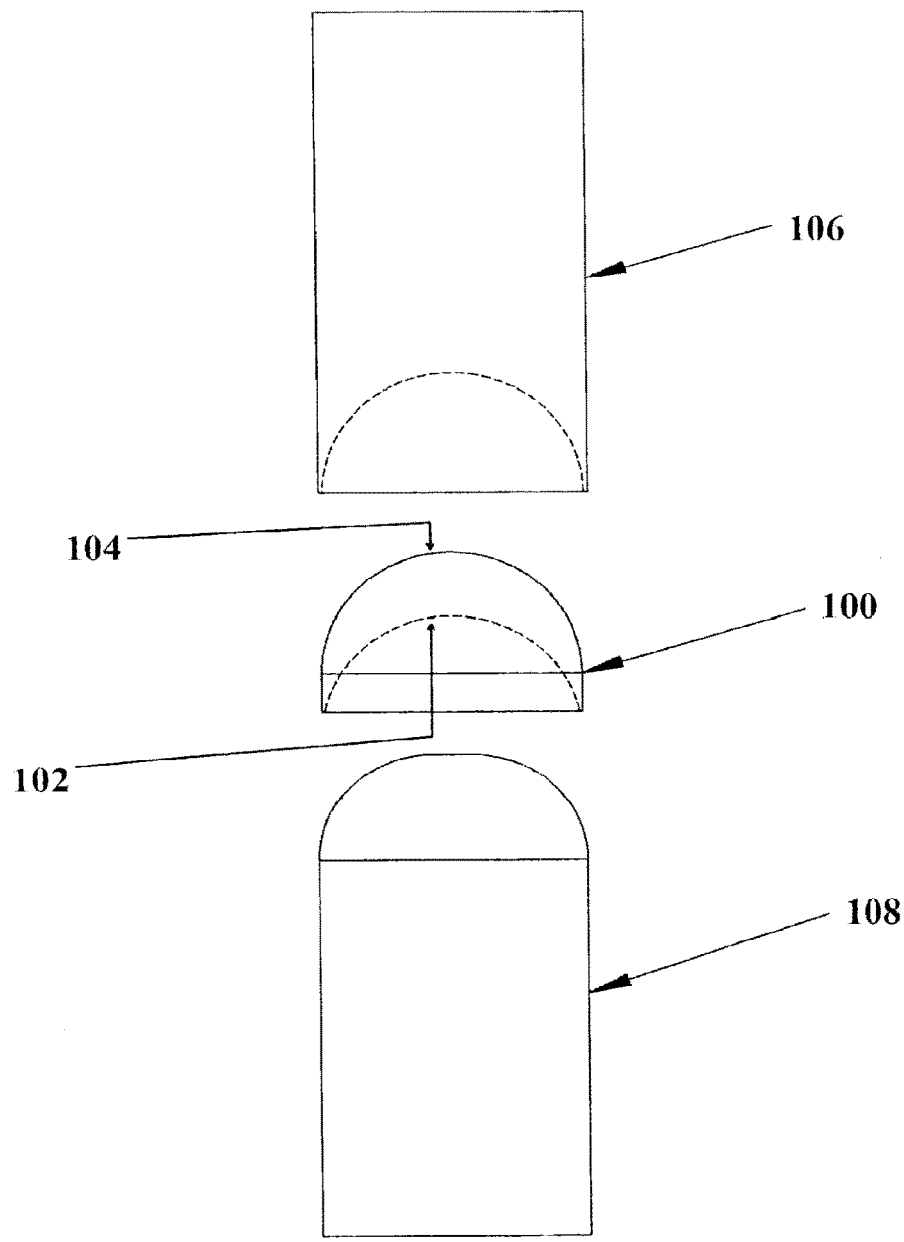
FIG. 20 is a side view of two prepared bone surfaces and a concave and convex shaped bone segment, in accordance with an aspect of the present invention.
Figure 21:
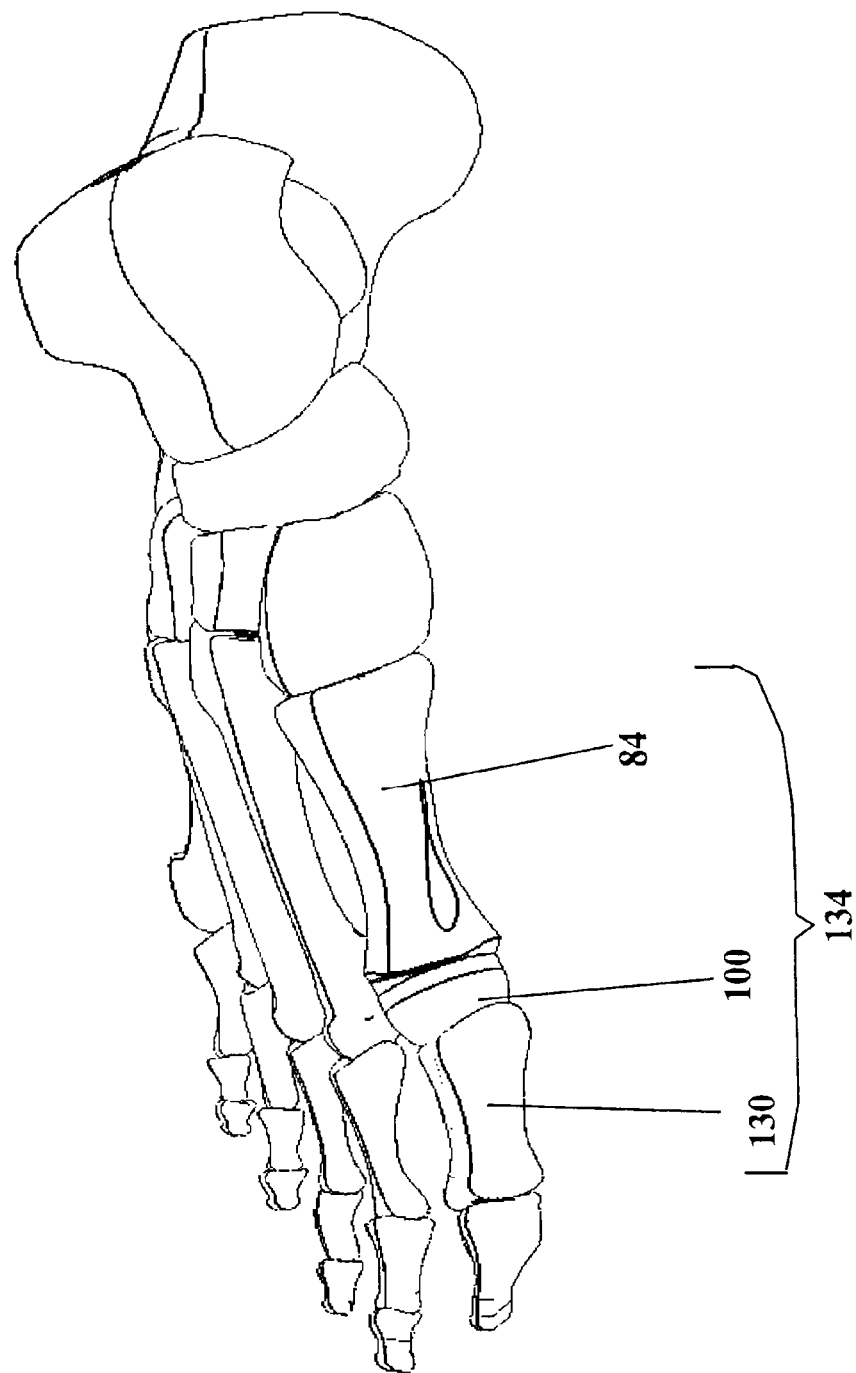
FIG. 21 is a medial view of a right foot having the bone segment of FIGS. 10A-10C implanted in the foot, in accordance with an aspect of the present invention.

Referring now to FIG. 20, the restoration bone segment 100 is shown aligned with the corresponding bones for implantation. The first bone being a concave bone 106 for mating with the convex end 104 of the bone segment 100 and the second bone being a convex bone 108 for mating with the concave end 102 of the bone segment 100. The cone reamer 110 and cup reamer 112 may have cutting edges 116 and 122, respectively, ranging for example from about 10 mm to 24 mm, with the most preferred dimensions for correction at the metatarsal-phalangeal joints being for example about 19 mm to 21 mm. As depicted in FIG. 21, the bone segment 100 may be inserted between the proximal phalanx 130 and the first metatarsal 84. In the depicted embodiment, the proximal end of the phalanx 130 is the concave bone 106 which mates with the convex end 104 of the bone segment 100, while the distal end of the first metatarsal 84 is the convex bone 108 which mates with the concave end 102 of the bone segment 100 to create a ball and socket configured metatarsal-phalangeal joint 134. By using an implant with a concave end 102 and a convex end 104 the amount of bone resection of the metatarsal-phalangeal joint 134 is minimized. In addition, the use of the bone segment 100 enables lengthening of the first metatarsal 84 before the metatarsal-phalangeal joint 134 is fused to help maintain a normal gait for the patient. The diameter of the bone segment 100 for use in the metatarsal-phalangeal joint 134 may range from for example about 10 mm to 24 mm, with the more preferable dimensions being for example about 19 mm to 21 mm. The thickness of the bone segment 100 for use in the metatarsal-phalangeal joint 134 may range from about 5 mm to about 20 mm for a bone segment 100. It is also contemplated that the bone segment 100 may be used in other joints and bones of the lower extremity, as well as in the joints and bones of the upper extremity.

Figure 24:
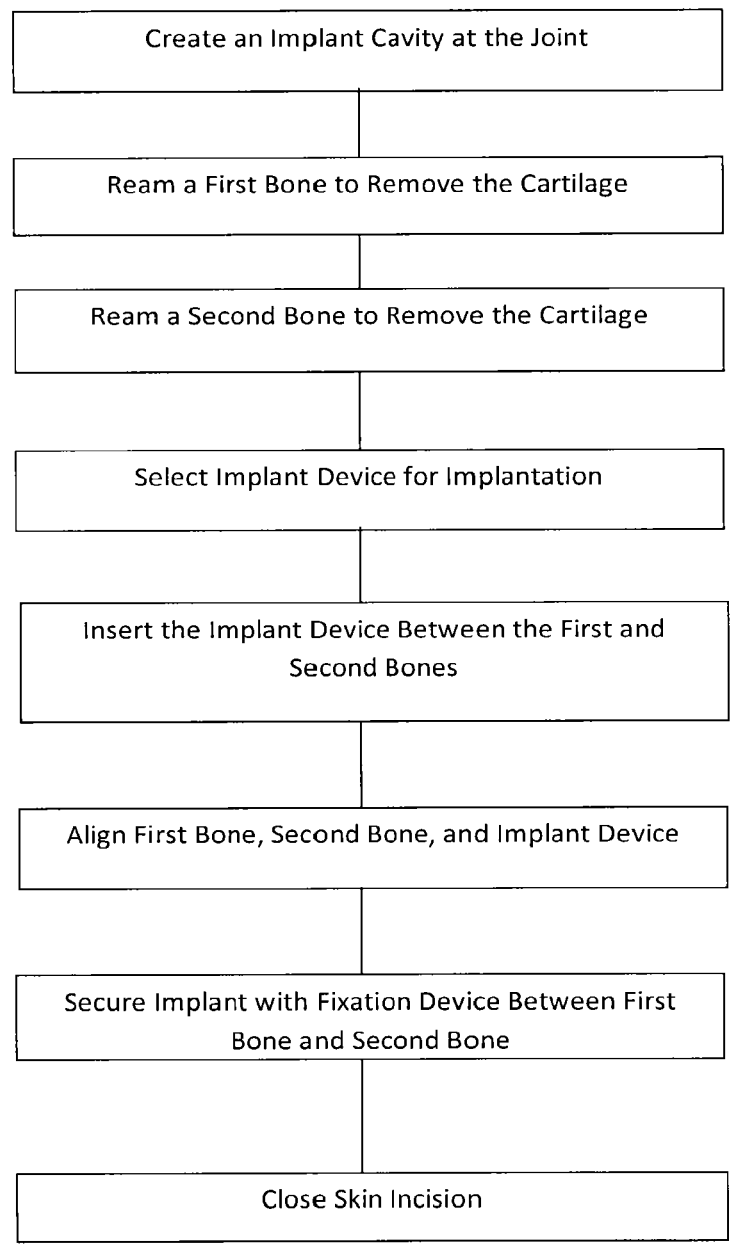
FIG. 24 depicts another embodiment of a surgical method for implanting an implant device into a patient's body, in accordance with an aspect of the present invention.

A surgical method for implanting the bone segment 100 into a joint, as seen in FIG. 24, will now be described. The method utilizes some of the devices, instruments, features, aspects, components, and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

Assuming the patient has a shortened bone which needs to be corrected, an implant device, such as bone segment 100, and a fixation member may be used to correct the deformity. The fixation member may include one or more plates, screws, wires, or external fixation. For example, the first metatarsal and phalanx may have been shortened due to several reasons, such as a hallux valgus deformity, a revision surgery due to a failed prior surgery, a non-union, or a generally short anatomy. All of these resulting in a shortened first metatarsal, which may be affecting the person's gait. As the phalanx and first metatarsal are being used for exemplary purposes only, the generic term "first bone" may be used hereinafter to refer to the phalanx bone, or any other bone that includes similar features, positioning, orientation, function or the like. Similarly, the generic term "second bone" may be used hereinafter to refer to the first metatarsal bone, or any other bone that includes similar features, positioning, orientation, function or the like. Likewise, the generic term "first joint" may be used hereinafter to refer to the joint between the phalanx and the first metatarsal, or any other joint that includes similar features, positioning, orientation, function or the like.

As best illustrated in FIG. 24, in order to correct the deformity in the first and second bones, an implant cavity will first be formed at the first joint, whereby the first joint is exposed and the first and second bones are prepared. The first bone may be prepared by reaming the first bone to remove the cartilage from the proximal surface of the first bone thereby giving the proximal end of the first bone a concave surface. Next, the second bone may be prepared by reaming to remove the cartilage from the distal surface of the second bone, thereby giving the proximal end of the second bone a convex surface. Once the first and second bones have been prepared, the surgeon may select a bone segment 100, having a concave end 102 and a convex end 104, from a kit containing a set of each of various sizes of bone segments 100 which have various circumferences and thicknesses. Alternatively, the surgeon may select a cylinder of bone from the kit having a desired circumference and use the cup reamer 112 and cone reamer 110 to cut a bone segment 100 for the desired site intra-operatively. The surgeon then inserts the convex end 104 of the bone segment 100 into the concave surface of the first bone and fits the concave end 102 of the bone segment 100 over the convex surface of the second bone. Alternatively, the concave end 102 of the bone segment 100 may be inserted over the convex surface of the second bone and then the convex end 104 of the bone segment 100 inserted into the concave surface of the first bone. Once the bone segment 100 has been inserted the combined length of the first and second bones will be increased and the first and second bones aligned to a desired position. After the two bones are aligned and a final position is determined, a removable fixation device, such as a guide wire, may be used to secure the bone segment 100 while additional fixation is applied. The additional fixation of the bone segment 100 may be accomplished with one or more plates, screws, wires, or external fixation devices. Once the bone segment 100 is secured within the first joint, the incision may be closed by the surgeon.

One advantage of the embodiments of the present invention discussed herein is that the bone segment 100 will allow for manipulation of the joint to provide optimal positioning prior to applying fixation. The metatarsal-phalangeal bone segment 100 having a concave end and a convex end allows the surgeon to precisely position the toe with dorsiflexion and valgus specifications without the requirement of additional bone resection. The bone segment 100 may be made from allograft or xenograft bone that is robust in cancellous structure and which has only been minimally processed to maintain maximum osteoinductivity.

Figure 22:
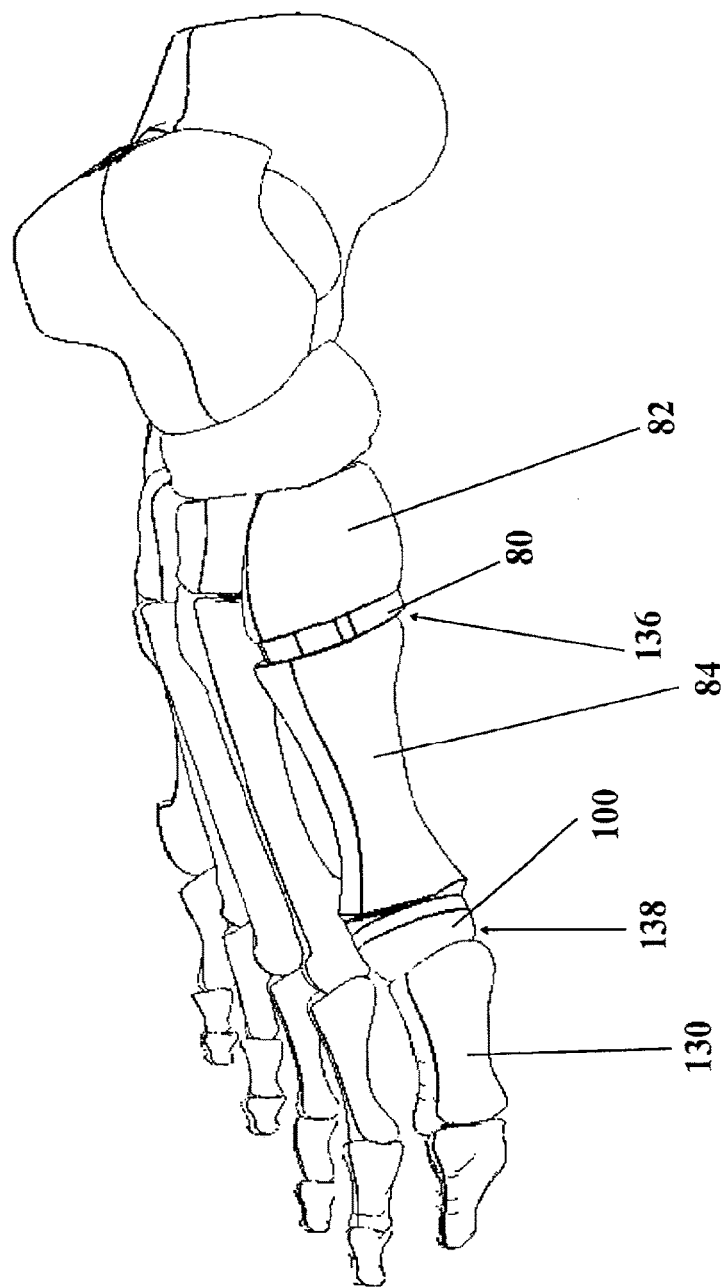
FIG. 22 is a medial view of a right foot having the bone segments of FIGS. 7A-7E and FIGS. 10A-10C implanted in the foot, in accordance with an aspect of the present invention.

An example of the placement of the bone wedge 80 of FIGS. 7A-7C and restoration bone segment 100 of FIGS. 10A-10C in the hallux are illustrated in FIG. 22. The restoration bone segment 100 may be used to adjust the length of the metatarsal-phalangeal joints or other similar joints in the upper and lower extremities. If length of the first metatarsal 84 is lost, the weight distribution on the patient's sesamoid bones may change which ultimately results in a change in how the patient walks. In order to address both the potential for functional loss of the sesamoid bones as well as a shortening of the phalanx, the present disclosure includes placement of the bone wedge 80 at the tarsal-metatarsal joint 136 and the restoration bone segment 100 at the metatarsal-phalangeal joint 138. The bone wedge 80 and the restoration bone segment 100 require additional fixation methods to secure them within the tarsal-metatarsal joint 136 and the metatarsal-phalangeal joint 138, respectively. Such fixation methods may include bone screws, wires, bone plates, external fixation, or the like. The bone wedge 80 and restoration bone segment 100 may also be used in other similar joints, for example the tarsal-metatarsal joints and metatarsal-phalangeal joints of the small toes as well as the metacarpo-phalangeal joint, carpo-metacarpal joint and other joints of the upper extremity. In addition, the bone wedge 80 may be used independently to correct deformities at the tarsal-metatarsal joint 136 and other similar joints in the upper and lower extremities. Likewise, the bone segment 100 may be used independently to correct deformities at the metatarsal-phalangeal joint 138 and other similar joints in the upper and lower extremities.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method of device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A surgical method for implanting a metatarsal-phalangeal implant with curved ends into a metatarsal-phalangeal joint, the method comprising:
    providing a monolithic metatarsal-phalangeal implant comprising a first end and an opposite second end;
    surgically exposing the metatarsal-phalangeal joint of a patient;
    separating a metatarsal bone from a proximal phalanx bone;
    obtaining a cone reamer;
    reaming the metatarsal bone with the cone reamer to form a convex end on the metatarsal bone for engaging the first end of the implant, the first end of the implant comprising a surface complementary to the convex end of the metatarsal bone;
    obtaining a cup reamer;
    reaming the proximal phalanx bone with the cup reamer to form a concave end on the proximal phalanx bone for engaging the second end of the implant, the second end of the implant comprising a surface complementary to the concave end of the proximal phalanx;
    inserting the metatarsal-phalangeal implant between the metatarsal bone and the proximal phalanx bone, wherein the first end of the implant is configured to mate with the convex end of the metatarsal bone and the second end of the implant is configured to mate with the concave end of the proximal phalanx bone, and
    securing the implant to the metatarsal bone and the proximal phalanx bone by positioning an external fixation device over the implant and attaching the fixation device to the metatarsal bone and the proximal phalanx bone,
    wherein the cone reamer comprises:
        a shank;
        a cutting portion coupled to a distal end of the shank with a plurality of cutting edges having a concave cutting surface; and
        a backstop received on the shank and positioned over the cutting portion to protect surrounding soft tissue from the cutting edges, and
    wherein the cup reamer comprises:
        a shank;
        a cutting portion coupled to a distal end of the shank with a plurality of cutting edges having a convex cutting surface; and
        a backstop received on the shank and positioned over the cutting portion to protect surrounding soft tissue from the cutting edges.

2. The method of claim 1, wherein the first end of the implant is a concave shape and the second end of the implant is a convex shape.

* * * * *